United States Patent [19]

Piran et al.

[11] Patent Number: 4,956,299

[45] Date of Patent: Sep. 11, 1990

[54] COMPLEMENT STABILIZATION

[75] Inventors: Uri Piran, Sharon; Milos Stastny, Ashland; Laura S. Uretsky, Milford, all of Mass.

[73] Assignee: Ciba Corning Diagnostics Corp., Medfield, Mass.

[21] Appl. No.: 316

[22] Filed: Dec. 31, 1986

[51] Int. Cl.$^5$ ............................................. G01N 33/54
[52] U.S. Cl. ........................................ 436/18; 436/16; 252/408.1
[58] Field of Search ...................... 436/8–18, 436/536, 537, 826, 829, 821; 435/4, 7, 177, 180, 182, 188, 810; 252/408.1

[56] References Cited

U.S. PATENT DOCUMENTS

| | | | |
|---|---|---|---|
| 3,629,142 | 12/1971 | Marbach | 436/18 |
| 3,682,835 | 8/1972 | Louderback | 436/18 |
| 4,350,659 | 9/1982 | Riceberg | 436/18 |
| 4,379,847 | 4/1983 | Fruitstone et al. | 436/8 |
| 4,404,285 | 9/1983 | Hou | 436/17 |
| 4,483,921 | 11/1984 | Cole | 436/536 |

Primary Examiner—Thomas Wallen
Attorney, Agent, or Firm—William G. Gosz; Nicholas I. Slepchuk, Jr.

[57] ABSTRACT

The present invention relates to a novel method for stabilizing aqueous solutions of serum complement for extended periods of time and the resultant stabilized complement solutions. More particularly, morphilino buffering compounds and tris-hydroxymethyl buffering compounds have been used to make aqueous buffers with a pH between about 6.5 and 8.5 and a concentration of greater than 0.01M. These buffers have been found to extend the normal life of complement solutions to unexpectedly longer periods.

16 Claims, No Drawings

COMPLEMENT STABILIZATION

TECHNICAL FIELD

The present invention relates to a novel method for stabilizing aqueous solutions of serum complement for extended periods of time and the resultant stabilized complement solutions. More particularly, morphilino buffering compounds and tris-hydroxymethyl buffering compounds have been used to make aqueous buffers with a pH between about 6.5 and 8.5 and a concentration of greater than 0.01M. These buffers have been found to extend the normal life of complement solutions to unexpectedly longer periods.

BACKGROUND ART

Serum complement (often referred to simply as complement) is known in the art to be a highly complex system of approximately at least nine different serum proteins found in mammals. In the body, complement operates in a cascade fashion to destroy the outer cellular membrane of an immunological-invading agent.

However, outside of the body it is highly unstable. Aqueous solutions of complement become useless within a day, even when stored at 4° C. In the past, complement was stabilized in two ways. It was either frozen or lyophilized.

The need for greater stability for complement solutions has increased because it is used now as a key component in diagnostic assays. For example, U.S. Pat. No. 4,483,921 to Francis X. Cole describes a liposome-based immunoassay which uses complement to lyze, i.e. break open, holes in the walls of liposomes. Before the present invention, the user of such an assay had to prepare their complement solutions daily in order to practice such an assay.

DISCLOSURE OF THE INVENTION

The present invention relates to a method for improving the stability of serum complement in an aqueous solution. Either a morphilino buffering compound, a tris-hydroxymethyl compound, or a combination thereof is added to the complement as an aqueous buffer, having a buffer concentration in the final buffered complement solution of greater than about 0.01M and a buffer pH of between about 6.5 and 8.5. These buffering compounds are conventional and well-known to those of skill in the art.

Complement solutions stabilized in this manner unexpectedly have a substantial portion of their activity remaining even after ninety hours of storage at 4° C. Moreover, for at least forty hours there is no loss in activity. The benefits of the present invention do not depend upon whether the complement is fresh, frozen, or lyophilized. Moreover, the addition of ionic salts to the present solution such that the solution contains at least 0.1 moles of an ionic species enhances the stability of complement even more.

The effective increase in the stability of complement solutions is not achieved with all buffers of equal pH and molar concentration. It has been found that phosphate buffers do not offer such stability.

MODES OF THE INVENTION

In a preferred embodiment, complement is added to an aqueous buffer having a pH of 7.5 and a molar concentration of 0.2M. Suitable morpholino buffering compounds include 3-(N-Morpholino)propane sulfonic acid (MOPS), 3-(N-Morpholino)-2-hydroxypropane sulfonic acid (MOPSO), and 2-(N-Morpholino)ethane sulfonic acid (MES). Suitable tris-hydroxymethyl (TRIS) buffering compounds include Tris-(hydroxymethyl)aminomethane (TRIS), Bis(2-hydroxyethyl)imino-tris-(hydroxymethyl)-methane (BIS-TRIS), N-Tris(hydroxymethyl)methyl-2-aminoethane sulfonic acid (TES), 3-[N-(Tris-hydroxymethyl)methylamino]-2-hydroxypropane sulfonic acid (TAPSO), N-Tris(hydroxymethyl)methyl glycine (TRICINE), and N-Tris(hydroxymethyl)methyl-3-aminopropane sulfonic acid (TAPS).

STABILITY TEST

A liposome immunoassay was devised which followed the homogeneous format disclosed in U.S. Pat. Nos. 4,483,921 and 4,342,826 to Cole. The analyte for these tests was the thyroid hormone thyroxine (known as $T_4$).

Liposomes derivatized by conventional methods containing an enzymatic developing reagent, glucose 6-phosphate dehydrogenase (G-6-PDH), were incubated with rabbit anti-$T_4$ antiserum for about seven minutes. Various aqueous complement solutions having a fixed, effective amount of complement were added to the above mixture. The enzymatic signal was developed using known substrates and measured by conventional spectrophotometer means at 340 nanometers.

EXAMPLE 1

Shorter-Term Stability

A number of buffers and other ionic compounds having an 0.2M concentration and a pH of 7.5 were made using a 1:1 dilution of complement to water. After 20 hours of storage at 4° C., the solutions were used in the above $T_4$ stability test fresh 1:1 complement in water dilution sans additives was used as a control. The activity was calculated as a percentage of the activity of the fresh complement solution.

As the results in Table 1 show, the morpholino and TRIS buffering compounds all displayed a high degree of activity, and thus, stability. While the acetate buffer also had a good short-term stability, lack of utility is shown in the longer-term stability tests in Example 2.

TABLE 1

| Remaining Activity of Complement Solutions on a Daily Basis ||
|---|---|
| Complement Diluent | Percent Activity |
| MOPS* | 116% |
| Na Acetate | 105% |
| Water (control) | 100% |
| MOPSO* | 88% |
| TRIS* | 83% |
| MES* | 78% |
| Phosphate | 75% |
| PIPES | 66% |
| Borate | 63% |
| Barbital | 45% |
| BES | 43% |
| HEPES | 42% |
| Bicine | 39% |
| EPPS | 37% |
| N-Acetyl Glycine | 30% |
| Di Water | 17% |
| Glycylglycine | 17% |
| Glycine | 14% |

*present invention

EXAMPLE 2

Longer-Term Stability

Essentially the same procedure in Example 1 was used except this time the solutions were diluted 1:4, made up in final molar concentrations of 0.1 and 0.2M strengths, and held in storage at 4° C. for 90 hours. Again, the results in Table 2 show the superior effect of the present invention.

TABLE 2

| Remaining Activity of Complement Solutions After Almost Four Days | | |
|---|---|---|
| Complement Diluent | | Percent Activity |
| MOPSO | 0.1 M | 14% |
| | 0.2 M | 69%* |
| TRIS | 0.1 M | 14% |
| | 0.2 M | 80%* |
| Acetate | 0.1 M | 15% |
| | 0.2 M | 15% |

*present invention

EXAMPLE 3

Effects of pH

Finally, the procedure described above was used to test the effects of pH on the present invention. In this case the solutions had a 0.2M concentration, used a 50:50 combination of MOPSO and TRIS, and the buffer pHs varied from 6.5 to 8.5. Storage times were 18 and 40 hours. The results in Table 3 show no significant difference in activity either between the solutions of varying pHs or storage times.

TABLE 3

| Remaining Activity of Complement Solutions Having Varying pHs | | |
|---|---|---|
| pH | Time | Percent Activity |
| 6.5 | 18 | 121% |
| | 40 | 134% |
| 7.5 | 18 | 130% |
| | 40 | 132% |
| 8.5 | 18 | 118% |
| | 40 | 122% |

In summation, the present invention represents an important advance in the ability to use liposome immunoassays on a commercial basis. Technicians no longer need to prepare solutions on an hourly or even a daily basis.

It should be apparent to one having ordinary skill in the art that many variations are possible without departing from the spirit and scope of the invention.

We claim:

1. A stabilized aqueous complement solution comprising complement, water, and a buffering compound selected from the group consisting of morpholino buffering compounds, tris-hydroxymethyl buffering compounds, and a combination of morpholino and tris-hydroxymethyl buffering compounds, wherein the final concentration of the buffering compound in the stabilized aqueous complement solution is greater than about 0.01M and the final pH of the stabilized aqueous complement solution is between about 6.5 and about 8.5.

2. The stabilized aqueous complement solution of claim 1 wherein the buffering compound is a morpholino buffering compound.

3. The stabilized aqueous complement solution of claim 2 wherein the final concentration of the morpholino buffering compound is 0.2M.

4. The stabilized aqueous complement solution of claim 2 wherein the morpholino buffering compound is selected from the group consisting of 3-(N-Morpholino) propane sulfonic acid, 3-(N-Morpholino)-2-hydroxypropane sulfonic acid, and 2-(N-Morpholino)ethane sulfonic acid.

5. The stabilized aqueous complement solution of claim 1 wherein the buffering compound is a tris-hydroxymethyl buffering compound.

6. The stabilized aqueous complement solution of claim 3 wherein the final concentration of the tris-hydroxymethyl buffering compound is 0.2M.

7. The stabilized aqueous complement solution of claim 3 wherein the tris-hydroxymethyl buffering compound is selected from the group consisting of Tris-(hydroxymethyl)aminoethane, Bis-(2-hydroxyethyl)imino-tris-(hydroxymethyl)methane, N-Tris-(hydroxymethyl)-2-aminoethane sulfonic acid, 3-[N-(Tris-hydroxymethyl)methylamino]-2-hydroxypropane sulfonic acid, N-Tris-(hydroxymethyl)methyl glycine, and N-Tris-(Hydroxymethyl)methyl-3-aminopropane sulfonic acid.

8. The stabilized aqueous complement solution of claim 1 wherein the complement has been frozen or lyophilized prior to addition to the stabilized aqueous complement solution.

9. A process for stabilizing complement which comprises adding to the complement an aqueous buffer comprising water and a buffering compound selected from the group consisting of morpholino buffering compounds, tris-hydroxymethyl buffering compounds, and a combination of morpholino and tris-hydroxymethyl buffering compounds, wherein the final concentration of the buffering compound in the aqueous buffer after addition to the component is greater than about 0.1M and the final pH of the aqueous buffer after addition to the complement is between about 6.5 and about 8.5.

10. The process of claim 9 wherein the buffering compound is a morpholino buffering compound.

11. The process of claim 10 wherein the final concentration of the morpholino buffering compound is 0.2M.

12. The process of claim 10 wherein the morpholino buffering compound is selected from the group consisting of 3-(N-Morpholino)propane sulfonic acid, 3-(N-Morpholino)-2-hydroxypropane sulfonic acid, and 2-(N-Morpholino)ethane sulfonic acid.

13. The process of claim 9 wherein the buffering compound is a tris-hydroxymethyl buffering compound.

14. The process of claim 13 wherein the final concentration of the tris-hydroxymethyl buffering compound is 0.2M.

15. The process of claim 13 wherein the tris-hydroxymethl buffering compound is selected from the group consisting of Tris-(hydroxymethyl)aminomethane, Bis(2-hydroxyethyl)imino-tris-(hydroxymethyl)methane, N-Tris(hydroxymethyl)methyl-2-aminoethane sulfonic acid, 3-[N-(Tris-hydroxymethyl)methylamino]-2-hydroxypropane sulfonic acid, N-Tris(hydroxymethyl)methyl glycine, and N-Tris(hydroxymethyl)methyl-3-aminopropane sulfonic acid.

16. The process of claim 9 wherein the complement has been frozen or lyophilized prior to addition of the aqueous buffer.